(12) United States Patent
Golan et al.

(10) Patent No.: US 11,980,483 B2
(45) Date of Patent: May 14, 2024

(54) METHOD AND SYSTEM FOR CARDIAC SIGNAL PROCESSING

(71) Applicant: Viz.ai Inc., San Francisco, CA (US)

(72) Inventors: David Golan, San Francisco, CA (US); Eli Goz, San Francisco, CA (US); Shelly Yehezkely, San Francisco, CA (US); Ruth Ann Forney, San Francisco, CA (US); Jacob Schiftan, San Francisco, CA (US); Christopher Mansi, San Francisco, CA (US); Clayton Eli Radakovich, San Francisco, CA (US)

(73) Assignee: Viz.ai Inc., San Francisco, CA (US)

( * ) Notice: Subject to any disclaimer, the term of this patent is extended or adjusted under 35 U.S.C. 154(b) by 0 days.

(21) Appl. No.: 18/209,936

(22) Filed: Jun. 14, 2023

(65) Prior Publication Data
US 2023/0397888 A1 Dec. 14, 2023

Related U.S. Application Data

(60) Provisional application No. 63/352,081, filed on Jun. 14, 2022.

(51) Int. Cl.
*G06K 9/00* (2022.01)
*A61B 5/00* (2006.01)
*A61B 5/366* (2021.01)
*G16H 50/70* (2018.01)

(52) U.S. Cl.
CPC ............ *A61B 5/7267* (2013.01); *A61B 5/366* (2021.01); *G16H 50/70* (2018.01); *A61B 5/7203* (2013.01)

(58) Field of Classification Search
None
See application file for complete search history.

(56) References Cited

U.S. PATENT DOCUMENTS

| | | | |
|---|---|---|---|
| 2010/0217143 A1 | 8/2010 | Whittington et al. | |
| 2019/0216350 A1 | 7/2019 | Sullivan et al. | |
| 2020/0160980 A1* | 5/2020 | Lyman | G06F 21/6254 |
| 2021/0224988 A1 | 7/2021 | Mansi et al. | |
| 2022/0384045 A1* | 12/2022 | Zimmerman | A61B 5/318 |

OTHER PUBLICATIONS

Hu, Jie, et al., "Squeeze-and-Excitation Networks", 2018 IEEE/CVF Conference on Computer Vision and Pattern Recognition, IEEE Computer Society.

* cited by examiner

*Primary Examiner* — Wei Wen Yang
(74) *Attorney, Agent, or Firm* — Jeffrey Schox; Caitlin Ploch

(57) ABSTRACT

A system for cardiac signal processing, preferably including any or all of: a data collection device, a set of computing and/or processing subsystems, a set of algorithms and/or models, and/or a set of output devices. A method for cardiac signal processing, preferably including processing a set of inputs to determine a set of metrics and determining a set of outputs based on the set of metrics and/or a set of supplementary metrics, and optionally including any or all of: receiving a set of inputs, determining a set of supplementary metrics associated with the set of metrics, and/or triggering the set of outputs.

20 Claims, 14 Drawing Sheets

Mobile application interface for recipient of outputs

METHOD AND SYSTEM FOR CARDIAC SIGNAL PROCESSING

CROSS-REFERENCE TO RELATED APPLICATIONS

This application claims the benefit of U.S. Provisional Application No. 63/352,081, filed 14 Jun. 2022, which is incorporated in its entirety by this reference.

TECHNICAL FIELD

This invention relates generally to the signals processing and triage fields, and more specifically to a new and useful system and method for cardiac signal processing in the signals processing and triage fields.

DETAILED DESCRIPTION

The following description of the embodiments of the invention is not intended to limit the invention to these embodiments, but rather to enable any person skilled in the art to make and use this invention.

1. Overview

Figure 1:
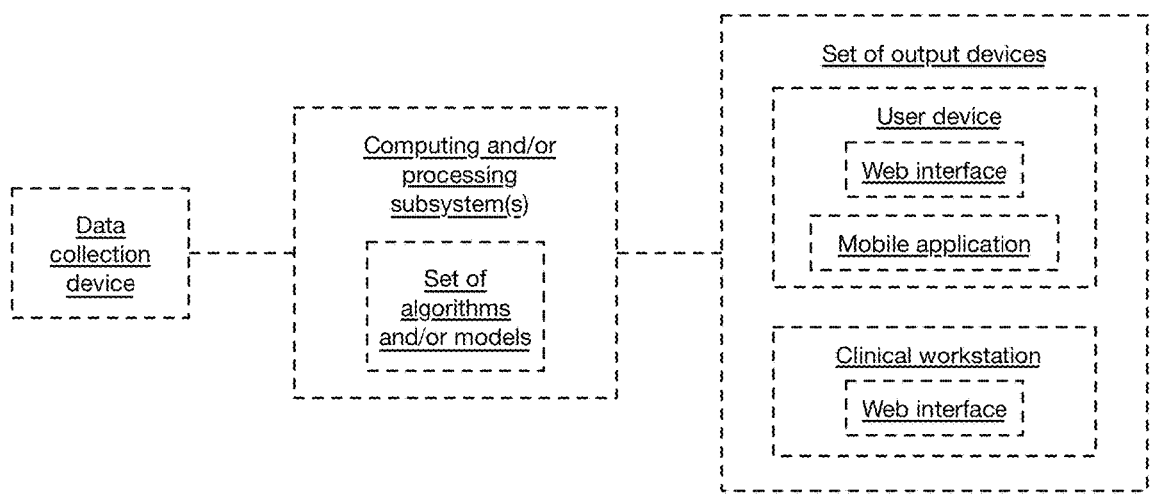
FIG. 1 is a schematic of a system for cardiac signal processing.

As shown in FIG. 1, a system 100 for cardiac signal processing can include any or all of: a data collection device, a set of computing and/or processing subsystems, a set of algorithms and/or models, a set of output devices, and/or any other components. Additionally or alternatively, the system can include and/or interface with any or all of the components as described in any or all of: U.S. application Ser. No. 16/012,458, filed 19 Jun. 2018, U.S. application Ser. No. 16/012,495, filed 19 Jun. 2018, U.S. application Ser. No. 16/913,754, filed 26 Jun. 2020, U.S. application Ser. No. 16/938,598, filed 24 Jul. 2020, U.S. application Ser. No. 17/001,218, filed 24 Aug. 2020, and U.S. application Ser. No. 16/688,721, filed 19 Nov. 2019, each of which is incorporated in its entirety by this reference.

Figure 2:
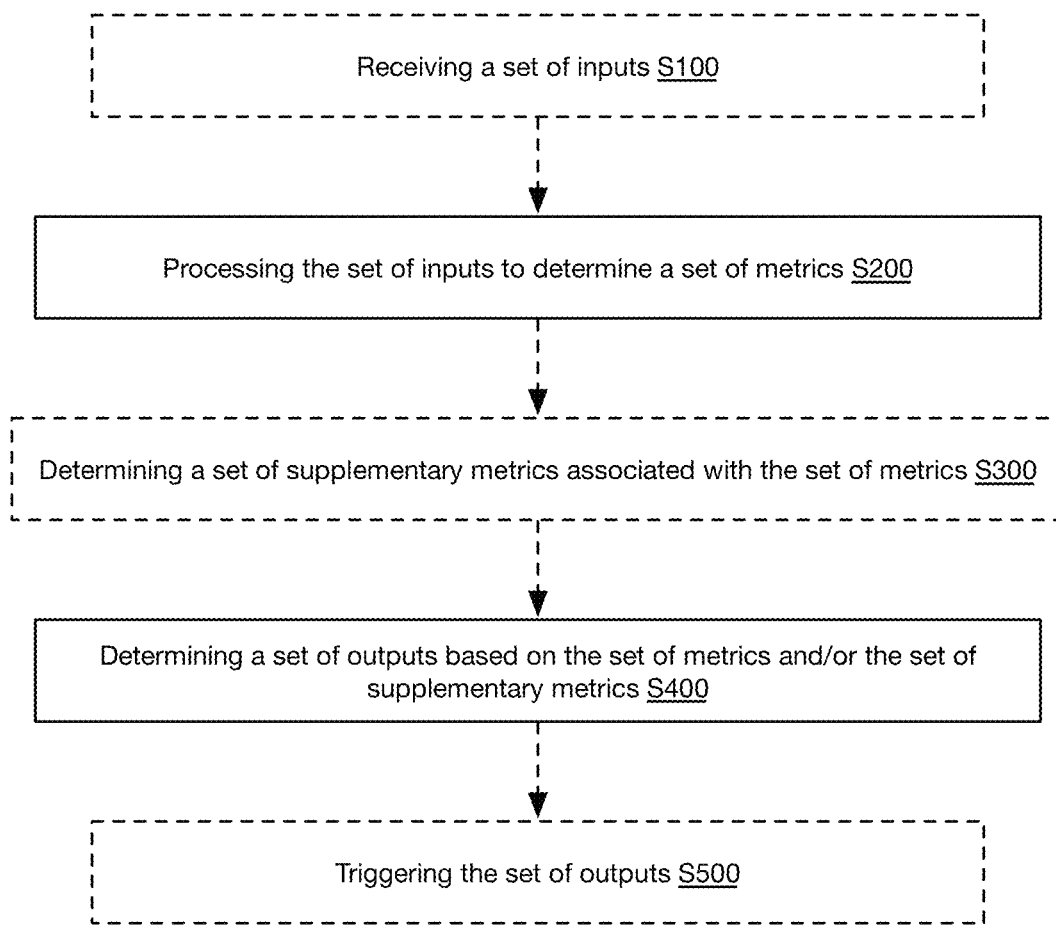
FIG. 2 is a schematic of a method for cardiac signal processing.

As shown in FIG. 2, a method 200 for cardiac signal processing includes processing a set of inputs to determine a set of metrics S200 and determining a set of outputs based on the set of metrics and/or a set of supplementary metrics S400. Additionally or alternatively, the method 200 can include any or all of: receiving a set of inputs S100; determining a set of supplementary metrics associated with the set of metrics S300; and triggering the set of outputs S500. Further additionally or alternatively, the method 200 can include and/or interface with any or all of the processes described in any or all of: U.S. application Ser. No. 16/012,458, filed 19 Jun. 2018, U.S. application Ser. No. 16/012,495, filed 19 Jun. 2018, U.S. application Ser. No. 16/913,754, filed 26 Jun. 2020, U.S. application Ser. No. 16/938,598, filed 24 Jul. 2020, U.S. application Ser. No. 17/001,218, filed 24 Aug. 2020, and U.S. application Ser. No. 16/688,721, filed 19 Nov. 2019, each of which is incorporated in its entirety by this reference, or any other suitable processes performed in any suitable order.

Figure 3A:
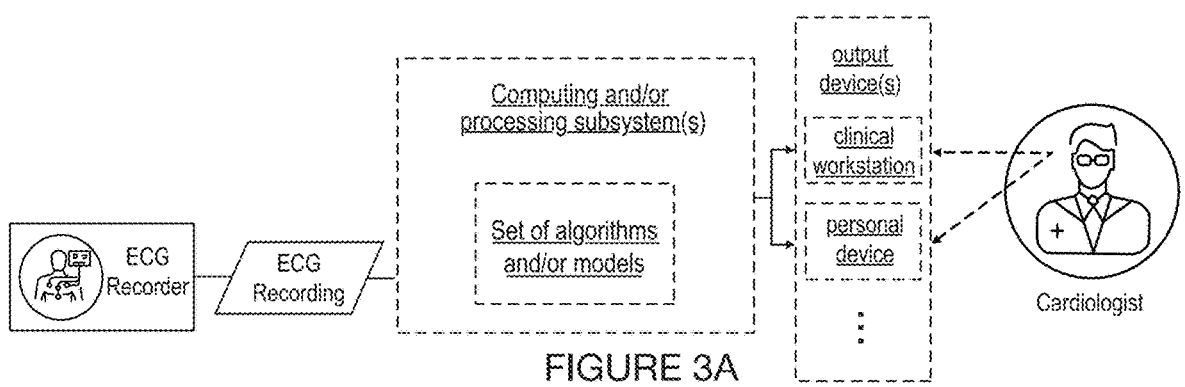
FIG. 3A depicts a schematic variation of a system for cardiac signal processing.
Figure 3B:
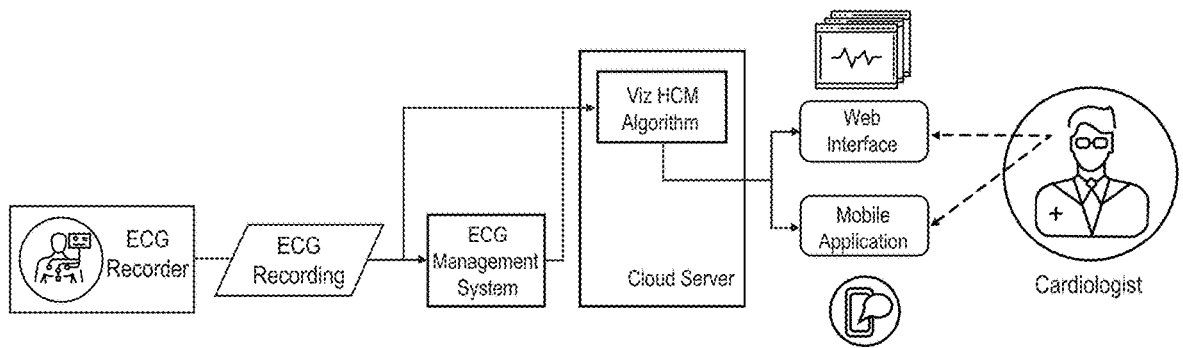
FIG. 3B depicts a schematic example of the system for cardiac signal processing.

The method 200 is preferably performed using the system 100 described above, such as shown by way of examples in FIGS. 3A, 3B, 5A, and/or 5B. However, the method can additionally or alternatively be performed using any other suitable system(s).

2. Technical Advantages

Variants of the technology can confer one or more advantages over conventional technologies.

First, variants of the technology can confer the advantage of providing early, robust, and reliable detections of hypertrophic cardiomyopathy (HCM) and optionally informing and/or executing optimal follow-up actions (e.g., triage, treatment, etc.) for patients associated with these detections. This can, in turn, function to provide/enable a new workflow in which HCM can be tested for and detected earlier than conventional methods of HCM detection, which are currently either at the time that the patient has a sudden and often fatal cardiac event and/or in the event that the patient undergoes a more complex diagnostic evaluation (e.g., echocardiography) which is closely evaluated by a cardiac expert.

Second, variants of the technology can additionally or alternatively confer the advantage of being implemented independently of (e.g., in parallel with) conventional standard of care pathways, which can function to prevent disruption of conventional standard of care pathways, provide an additional pathway to detection (e.g., for redundancy, in the event of a false negative, etc.), and/or can confer other benefits. In a set of specific examples, the technology is configured to identify patients for further HCM follow-up without replacing the current standard of care methods for diagnosis of HCM.

Third, variants of the technology can additionally or alternatively confer the advantage of preventing negative consequences which may result from false positive determinations, which can include, for instance: burden on the user being notified of such determinations (e.g., resulting in notification fatigue), the wasting of time and/or resources (e.g., in further analyzing the patient associated with the false positive), the ignoring of true positives (e.g., due to an overwhelming percentage of false positives in the overall determinations), and/or other consequences. This can be particularly challenging as well as detrimental for conditions which have a very low prevalence, such as HCM. In a set of specific examples, the technology confers the benefit of determining and displaying confidence levels associated with determinations such that users (e.g., specialists) can assess and/or recommend next steps for patients accordingly.

Fourth, variants of the technology can additionally or alternatively confer the advantage of minimizing and/or preventing the occurrence of missed cardiac conditions, such as HCM, in which negative and/or fatal outcomes which can happen suddenly in absence of detection. For instance, in cases of HCM, even if an ECG is performed, the condition (and/or ECG patterns suggestive of possible presence of the condition) may be missed for a variety of reasons (e.g., person reviewing ECG is not looking specifically for patterns suggestive of possible HCM; person reviewing ECG is not trained to detect HCM and/or patterns suggestive of possible HCM; as compared with variants of the technology, human review of ECG may be less capable of detecting patterns suggestive of possible HCM; etc.). In particular, non-cardiologist physicians reviewing a patient's ECG may miss signs that would be recognized by cardiologists for further HCM assessment. By engaging cardiologists in the review and identification of patients who should receive additional follow up for HCM through implementation of the system and/or method, patients are more likely to receive follow-up for a condition that is treatable and manageable but can be fatal if left untreated.

Fifth, variants of the technology can additionally or alternatively confer the advantage of reducing data access and/or transfer requirements, such as reducing demand for medical history data. Some variants of the technology may utilize filtering based on patients' medical history to reduce false positive rates associated with the technology (e.g., by excluding patients whose medical history includes diagnoses and/or other conditions that may induce higher rates of false positives). In some examples, this medical history-based filtering can be deferred until after signal-based detection is performed (e.g., wherein the medical history-based filtering is performed only for signals resulting in a positive detection). Accordingly, medical histories may be needed only for patients whose signals result in positive detections, rather than requiring medical history data for all signals analyzed by the technology, thus reducing the data access and/or transfer requirements associated with these medical histories.

However, further advantages can additionally or alternatively be provided by the system and method disclosed herein.

3. System 100

The system 100 functions to provide a platform with which to assess a patient, and determine (e.g., quickly determine) and/or execute on an optimal treatment plan for a patient (e.g., presenting with an acute condition) based on the assessment. Additionally or alternatively, the system 100 can function to: enable the most qualified users to review data (e.g., cardiac experts remotely review data for suspected HCMs), efficiently transmit information to one or more users, alert users to important and/or critical information (e.g., while preventing notification fatigue), establish communication between users, enabling the sharing (e.g., confidential sharing, HIPAA-compliant sharing, de-identified sharing, etc.) of information between users, form and/or initiate a care team for the patient, assign the patient to one or more users and/or care teams, trigger one or more other actions (e.g., selection of a medical device, assignment of patient to a clinical trial, transfer of patient to another point of care, etc.), manage and check in on follow-up for the patient, and/or can perform any other functions.

Additionally or alternatively, the system 100 can function to process (e.g., with artificial intelligence [AI], machine learning, deep learning, etc.) a set of inputs (e.g., ECG data) in order to detect one or more suspected conditions and/or can perform any other suitable functions.

The system can include and/or interface with a set of data collection devices, which function to collect information associated with the patient and/or any other users (e.g., as described in S100). The set of data collection devices can include one or more biosignal detection devices, such as one or more cardiac devices (e.g., ECG/EKG monitor, such as 12-lead ECG, 8-lead ECG, ambulatory ECG such as Holter ECG, etc.). In a preferred set of variations, for instance, the data collection device includes an 8- or 12-lead ECG device. In a set of specific examples, the system enables receiving 8- or 12-lead ECGs in digital format, either directly from an ECG device or from an ECG management system. The ECG device or management systems are configured to automatically forward ECG data to a virtual machine installed on premises at a $1^{st}$ point of care that receives the ECG data and uploads it to a cloud server over a secure connection, where it is then analyzed.

Additionally or alternatively, the data collection devices can include one or more imaging (e.g., ultrasound, CT, MRI, etc.) devices and/or other diagnostic devices, user devices (e.g., mobile user devices), and/or any other devices.

The system 100 can include and/or interface with a set of computing and/or processing subsystems, which function to perform any or all of the processes of the method 200.

The computing system can include a remote computing system (e.g., cloud-based computing system), a local computing system (e.g., at a local server, onboard a mobile device or other device, etc.), or any combination of computing and/or processing systems at any suitable location(s).

In preferred variations, at least a portion of the method 200 is performed at a remote computing system (e.g., cloud-based), but additionally or alternatively any or all of the method 200 can be performed at a local computing subsystem.

The computing and/or processing subsystems can additionally include and/or interface with any or all of: routers (e.g., operating as a virtual machine, associated with a data collection device, coupled to and/or in communication with a data collection device, etc.), servers, data storage, and/or any other components.

The computing and/or processing subsystems further preferably interface with (e.g., include, store, etc.) and function to implement a set of algorithms and/or models, which are used in performing any or all of the processes of the method 200. The set of models and/or algorithms preferably includes machine learning algorithms (e.g., deep learning algorithms, neural networks, etc.), but can additionally or alternatively include rule-based models and/or algorithms, decision trees, lookup tables, a combination of tools, and/or any other tools.

The models can include classical or traditional approaches, machine learning approaches, and/or be otherwise configured. The models can include regression (e.g., linear regression, non-linear regression, logistic regression, etc.), decision tree, LSA, clustering, association rules, dimensionality reduction (e.g., PCA, t-SNE, LDA, etc.), neural networks (e.g., CNN, DNN, CAN, LSTM, RNN, ResNet, encoders, decoders, deep learning models, transformers, etc.), ensemble methods, optimization methods, classification, rules, heuristics, equations (e.g., weighted equations, etc.), selection (e.g., from a library), regularization methods (e.g., ridge regression), Bayesian methods (e.g., Naiive Bayes, Markov), instance-based methods (e.g., nearest neighbor), kernel methods, support vectors (e.g., SVM, SVC, etc.), statistical methods (e.g., probability), comparison methods (e.g., matching, distance metrics, thresholds, etc.), deterministics, genetic programs, and/or any other suitable model. The models can include (e.g., be constructed using) a set of input layers, output layers (e.g., single neuron with sigmoid activation), and hidden layers (e.g., connected in series, such as in a feed forward network;

connected with a feedback loop between the output and the input, such as in a recurrent neural network; etc.; wherein the layer weights and/or connections can be learned through training); a set of connected convolution layers (e.g., in a CNN); a set of self-attention layers; and/or have any other suitable architecture.

Models can be trained, learned, fit, predetermined, and/or can be otherwise determined. The models can be trained or learned using: supervised learning, unsupervised learning, self-supervised learning, semi-supervised learning (e.g., positive-unlabeled learning), reinforcement learning, transfer learning, Bayesian optimization, fitting, interpolation and/or approximation (e.g., using gaussian processes), back-propagation, and/or otherwise generated. The models can be learned or trained on: labeled data (e.g., data labeled with the target label), unlabeled data, positive training sets (e.g., a set of data with true positive labels, negative training sets (e.g., a set of data with true negative labels), and/or any other suitable set of data.

Any model can optionally be validated, verified, reinforced, calibrated, or otherwise updated based on newly received, up-to-date measurements; past measurements recorded during the operating session; historic measurements recorded during past operating sessions; or be updated based on any other suitable data.

Any model can optionally be run or updated: once; at a predetermined frequency; every time the method is performed; every time an unanticipated measurement value is received; or at any other suitable frequency. Any model can optionally be run or updated: in response to determination of an actual result differing from an expected result; or at any other suitable frequency. Any model can optionally be run or updated concurrently with one or more other models, serially, at varying frequencies, or at any other suitable time.

The models preferably include one or more validation models and detection models. However, the models can additionally or alternatively include any other suitable models.

The validation model(s) preferably function to validate the input data for use with the detection model(s). The validation models can include one or more inclusion/exclusion criteria filters ("criteria-based filter models), signal quality filters ("quality models", and/or other filters (and/or any other suitable models).

In some embodiments, the validation model(s) can include one or more models configured to assess and/or filter the input data (and/or associated information) based on a set of one or more criteria (e.g., inclusion and/or exclusion criteria). In some examples, these criteria can include excluding input data based on metadata-derived information, such as patient age (e.g., age less than 18 years or another minimum threshold, patient age not included in metadata and/or otherwise not known, etc.), missing metadata information (e.g., absence of one or more ECG technical parameters used to pre-process the input data), incompatibility indicated by metadata (e.g., absence of indication that ECG was collected using compatible equipment such as equipment manufactured by an approved manufacturer, indication of patient condition incompatible with detection such as presence of a pacemaker device, etc.). Additionally or alternatively, these criteria can include excluding input data based on ECG signal characteristics, such as ECG signal duration (e.g., duration less than 3, 5, 7, 10, 15, or 20 seconds or another minimum threshold), ECG signal sampling rate (e.g., rate less than 100, 200, 300, 500, 750, or 1000 Hz or another minimum threshold), ECG lead corruption and/or absence (e.g., signal present for fewer than 12 leads or 12 non-corrupted leads, signal present for fewer than 8 independent physical leads or 8 non-corrupted independent physical leads, signal absent and/or corrupted for too many leads to enable accurate reconstruction of signals from 8 independent physical leads and/or signals from all 12 leads, signal absent and/or corrupted for more than any other suitable missing/corrupted signal threshold, etc.), and/or any other suitable information. However, these models can additionally or alternatively be configured to assess and/or filter the input data based on any other suitable criteria.

In some embodiments, the validation model(s) can additionally or alternatively include one or more models configured to assess the input data quality (e.g., quality model(s)). These models can be configured to assess signal quality based on one or more signal quality indices (e.g., such as described in Liu, C. and Li, J. eds., 2020, Feature engineering and computational intelligence in ECG monitoring, Springer, which is herein incorporated in its entirety by this reference), such as lead absence/fall detection (e.g., zero-line detection for more than a threshold portion of the signal duration, such as 60%, 70%, 75%, 80%, 85%, 90%, 95%, etc., and/or absence of zero-line detection for less than a threshold time period, such as wherein the remaining signal duration in which no zero-line is detected is less than a threshold duration such as 0.5, 1, 1.5, 2, 2.5, 3, 3.5, or 4 seconds, etc.), time-domain quality indices (e.g., signal distribution skewness and/or kurtosis, standard deviation of the signal, etc.), frequency-domain quality indices (e.g., relative power in baseline, power spectrum distribution, low frequency power spectrum distribution, main frequency power spectrum distribution, high frequency power spectrum distribution, duration of ECG excerpts with outlier power spectrum distribution, etc.), quality indices based on QRS waves (e.g., comparison of beat detectors), and/or any other suitable quality indices. In some examples, the validation model(s) include one or more models (e.g., random forest classifier) trained to detect low-quality input data (e.g., based on one or more of the quality indices described above and/or based on any other suitable indicia of quality), preferably wherein these model(s) function to classify input ECG signals as either having acceptable quality or unacceptably low quality (e.g., wherein signals of unacceptably low quality are preferably rejected, rather than being provided as input to the detection model). For example, the validation model(s) can include a random forest classifier trained via supervised training (e.g., using a corpus of ECG signals labeled as either low quality or acceptable quality).

Additionally or alternatively, the quality model(s) can include one or more models configured to reject input data indicative of medical conditions that are incompatible with use of the detection model. In some examples, the quality model(s) can include a pacemaker presence model configured to detect whether an ECG signal is indicative of the presence of a pacemaker (e.g., wherein the model is trained via supervised training, preferably using a corpus of ECG signals labeled as indicative of pacemaker presence or pacemaker absence). For example, the pacemaker presence model (and/or any other suitable model for detecting incompatible medical conditions) can include one or more neural networks, preferably a convolutional neural network such as network including one or more temporal-domain convolution layers and/or spatial convolution layers (e.g., including a plurality of temporal-domain convolution layers followed by one or more spatial convolution layers), optionally along with one or more fully-connected layers, output layers (e.g., single neuron with sigmoid activation), and/or any other suitable layers.

In some embodiments, the validation model(s) can additionally or alternatively include one or more medical history models configured to assess the medical history of the patient (and/or any other suitable information associated with the patient) from which the ECG signal was sampled (e.g., configured to exclude input data associated with one or more patient diagnoses and/or conditions with which the detection model is incompatible and/or which may be associated with unacceptable increases in detection model false positive rate). For example, such a model (or models) can be configured to detect indications that the patient is associated with one or more diagnoses and/or conditions such as: hypertensive diseases, valve diseases (e.g., aortic stenosis, mitral valve disorders, etc.), non-HCM left ventricular hypertrophy (e.g., associated with hypertension), non-HCM cardiomyopathies, infiltrative and/or connective tissue disorders (e.g. amyloidosis, Anderson-Fabry, Friedreich ataxia, etc.), substance abuse, and/or postoperative condition (e.g., within a threshold time window following any operation or one or more specific operations or kinds of operations, at any point in time following one or more specific operations or kinds of operations, etc.). In examples, this model (or models) can include a text-matching model (e.g., based on regular expressions), a language model (e.g., large language model, such as a model trained and/or fine-tuned to detect such indications and/or instructed in context to detect such indications, etc.), and/or any other suitable model structure(s).

However, the system can additionally or alternatively include any other suitable validation models of any suitable kinds and/or having any other suitable functionalities.

The detection model(s) preferably function to detect possible indicia of one or more medical conditions. For example, the detection models can function to determine whether input data (e.g., ECG data) may be indicative of the presence (and/or likelihood of the presence) of one or more medical conditions (e.g., HCM). In some examples, the detection model includes a plurality of sub-models (e.g., trained neural networks), and can optionally include one or more aggregators (e.g., which can function to aggregate the outputs from the different sub-modules).

Some or all of the detection sub-models preferably accept the input data as an M×N tensor, wherein M is the number of leads represented in the input data, such as M=8 for the 8 independent physical of a 12-lead ECG (I, II, $V_1$, $V_2$, $V_3$, $V_4$, $V_5$, & $V_6$, wherein other leads, such as III, aVR, aVL, & aVF are linear combinations of two or more physical leads and so may be omitted from the analysis) and N is the number of signal values in each lead of the ECG signal (e.g., for a 500 Hz sampling rate and a signal duration of 10 seconds, N=500/s*10s=5000). However, some or all of the detection sub-models may additionally or alternatively accept the input data as one or more images (e.g., M images of identical dimension, one for each of the M leads represented in the input data; a single image representative of all M leads of the input data; etc.) and/or in any other suitable form(s). In some examples, one or more sub-models may additionally or alternatively accept metadata as input data (e.g., wherein some or all such sub-models may employ late fusion of metadata with the ECG signal data, such as wherein the sub-model includes a number of upstream layers that operate based only on the ECG signal data, followed by a downstream layer that ingests the metadata and fuses it with the outputs from the upstream layers). However, the sub-models can additionally or alternatively accept any other suitable inputs.

The detection model(s) preferably include one or more trained models. In some embodiments, the trained models can include one or more residual neural networks (ResNets). In some examples, one or more detection sub-models can include a residual neural network such as described in Hu, J., Shen, L., & Sun, G. (2018), "Squeeze-and-excitation networks," *Proceedings of the IEEE conference on computer vision and pattern recognition* (pp. 7132-7141), which is herein incorporated in its entirety by this reference. In some examples, one or more detection sub-models can include a series of one or more ResNet blocks, wherein some or all such ResNet blocks can include any or all of: batch normalization layers, activation layers (e.g., ReLu), convolution layers, squeeze and excite layers, stochastic depth layers (e.g., wherein one or more ResNet blocks may be bypassed during training via its stochastic depth layer), and/or any other suitable layers. The detection sub-models can additionally or alternatively include (e.g., following the ResNet blocks) one or more pooling layers (e.g., global average pooling layer), dropout layers, fully connected layers, output layers (e.g., single neuron with sigmoid activation), and/or any other suitable layers.

In some embodiments, some or all of the models can be trained via supervised training (e.g., based on a corpus of labeled input data, wherein the labels are indicative of the presence or absence of HCM and/or other medical condition(s), the presence or absence of indicia of possible HCM and/or other medical condition(s), and/or any other suitable information associated with HCM and/or other medical condition(s), etc.). In some examples, training of the model(s) includes employing one or more techniques that selectively ignore portions of the model (e.g., drop out techniques, bypass techniques, stochastic techniques, etc.). For example, during training, ResNet blocks may be bypassed (e.g., via skip connections, such as implemented in stochastic depth layers), which can function to reduce and/or avoid vanishing gradients and/or loss of information during a forward pass, and/or units of some or all of the final layers (e.g., of a pooling layer, such as a pooling layer preceding the fully connected output layer) may be dropped out to zero and/or otherwise modified, which can function to reduce and/or avoid overfitting during training. Such techniques are preferably stochastic techniques (e.g., wherein the blocks to be bypassed and/or units to be dropped out are selected randomly), but can additionally or alternatively include making training decisions, such as bypass and/or drop out selections, in any other suitable manner.

In some embodiments (e.g., in which the detection model includes a plurality of sub-models, such as an ensemble of trained neural networks), the system can include an aggregator. The aggregator preferably functions to aggregate outputs from the different sub-models (e.g., trained neural networks, such as ResNets) of the detection model (e.g., to generate a single detection score or classification based on the outputs of the different sub-models. In a first example, the aggregator generates an average of the results of each sub-model of the detection model. In a second example, the aggregator generates a weighted average of the results of each sub-model, such as a weighted average generated using learned weights (e.g., from a trained metalayer). In a third example, the aggregator discards one or more outlier values (e.g., maximum and/or minimum value, any value deviating from a measure of central tendency by more than a threshold amount, etc.) from the sub-models before generating an aggregation of the remaining (inlier) values, such as the mean of the inlier values. In a fourth example, the aggregator provides the maximum value, minimum value, median value, and/or any other suitable value associated with the set of sub-model outputs. However, the aggregator can additionally or alternatively aggregate the outputs from the different sub-models in any other suitable manner.

However, the system may additionally or alternatively include any other suitable detection model(s).

In some embodiments, the system may additionally or alternatively include one or more signal preprocessors (and/or any other suitable elements for input data preprocessing). The signal preprocessor preferably functions to accept the input data (e.g., as received from the ECG source and/or other source, after filtering and/or modification by some or all of the validation models, etc.) and modify it for provision to the detection sub-models (and/or for provision to the validation models and/or any other suitable elements of the system). For example, the system can include a signal preprocessor that includes a signal transformer and one or more reconfiguration elements (e.g., tensorfication element, image-generation element, etc.). The signal transformer can be configured to: select the signals corresponding to the relevant/desired leads (e.g., the 8 independent physical of a 12-lead ECG, being leads I, II, $V_1$, $V_2$, $V_3$, $V_4$, $V_5$, & $V_6$, wherein other leads, such as III, aVR, aVL, & aVF, are linear combinations of two or more physical leads and so may be omitted from the analysis), resample the signal to a desired sampling rate (e.g., 500 Hz), select a desired time window from the sample (e.g., select a time window of fixed duration, such as 10 seconds, which may be achieved by truncating the signal to the desired duration, by selecting a high-quality time window of the desired duration from the signal, and/or by selecting any other suitable time window from the signal), applying one or more signal filters (e.g., which can function to increase the fidelity of the ECG signal and/or the quality of the resulting analysis performed by the detection model) such as a denoising filter (e.g., bandpass filter, such as with a passband bounded by 0.5 Hz and/or 100 Hz) and/or baseline wander removal filter, and/or otherwise transforming the input data. The reconfiguration element can function to convert the input signal (and/or transformed signal) into a desired input format for each model of the detection model (e.g., a single multichannel tensor, set of single-channel tensors, single multichannel image, set of single-channel images, etc.) and/or for any suitable subset thereof. The reconfiguration element can receive the transformed signal from the signal transformer (e.g., wherein the reconfiguration element then outputs the signal to the detection model), can receive the input signal and then provide the tensor to the signal transformer (e.g., wherein the signal transformer then outputs the signal to the detection model), and/or can have any other suitable dataflow arrangement relative to the signal transformer (e.g., arranged between portions of the signal transformer, such as following lead selection but preceding bandpass filtering). In some examples (e.g., in which different models of the detection model accept different input data formats), the signal preprocessor can include multiple reconfiguration elements (e.g., arranged in parallel, such as all accepting the same data and each generating output data in a different format, such as for provision to a different model of the detection model). However, the signal preprocessor can additionally or alternatively include any other suitable elements in any suitable arrangement.

In a preferred set of variations, software (e.g., models, algorithms, etc.) is hosted on a cloud-based server, such as wherein 12-lead ECG sources (e.g., ECG machines or ECG information systems) will be configured to automatically send all ECG recordings acquired during clinical practice (or any suitable subset thereof) to a cloud-based server (e.g., without user intervention or decision-making). Once the ECG recordings have been received in the cloud, they are optionally automatically validated for analysis (e.g., inspected for inclusion/exclusion criteria and/or signal quality), and analyzed by the software algorithm. In specific examples, the software algorithm is preferably a machine-learning based algorithm that analyzes the received ECG recordings for characteristics/patterns suggestive of hypertrophic cardiomyopathy (HCM) and identifies the suspicious ECGs for further review.

The system can further include and/or interface with a set of output devices, which can function to: provide information to users (e.g., cardiac specialists), collect information from users (e.g., read receipt indicating that recipient has received a notification, recommended next steps for the patient, etc.), facilitate communication among users (e.g., members of a care team, the specialist and the patient, clinical trial coordinators and specialists, etc.), and/or perform any other functions.

The system can further include and/or interface with one or more applications (e.g., clients, client applications, client application executing on a device, etc.), which individually or collectively function to provide the outputs (e.g., from the remote computing system) to a user at an output device. Additionally or alternatively, the applications can individually or collectively function to receive one or more inputs from a user, provide one or more outputs to a healthcare facility (e.g., first point of care, second point of care, etc.) and/or a database associated with the healthcare facility (e.g., EMR, EHR, PACS, etc.), establish communication between users, send alerts and/or notifications to users, and/or perform any other suitable function.

The application is preferably configured to be executed on a mobile device (e.g., with any or all of the processing performed at a remote computing system such as a cloud-based computing system, with any or all of the processing performed at the mobile device, any combination, etc.) of the user, such as a phone, tablet, smart watch, and/or any other mobile device. The mobile device can be personal user device of the user, a device owned by the healthcare facility, and/or any other device. The application can further be configured to execute on any other devices, such as a workstation of the healthcare facility and/or any other devices. In specific examples, for instance, an application is executed on a mobile device with which the user can interact (e.g., for viewing images and/or reconstructions, for manipulating images and/or reconstructions, for communicating with other users, for receiving user inputs, etc.), wherein processing associated with the application is preferably performed at least partially at a cloud-based computing system. Additionally or alternatively, any or all of the processing can be performed at the mobile device.

The outputs provided at the application can include any or all of: an alert or notification (e.g., push notification, text message, call, email, etc.); biosignals or other inputs; a worklist (e.g., list of patients presenting for and/or requiring care, patients being taken care of by specialist, patients recommended to specialist, procedures to be performed by specialist, etc.); a set of patient lists (e.g., as described below); a messaging platform (e.g., HIPAA-compliant messaging platform, texting platform, video messaging, group messaging etc.); a telecommunication platform (e.g., video conferencing platform); a directory of contact information (e.g., $1^{st}$ point of care contact info, $2^{nd}$ point of care contact info, etc.); tracking of a workflow or activity (e.g., real-time or near real-time updates of patient status/workflow/etc.);

analytics based on or related to the tracking (e.g., predictive analytics such as predicted time remaining in radiology workflow or predicted time until stroke reaches a certain severity; average time in a workflow; average time to transition to a second point of care, etc.); or any other suitable output.

The application preferably includes and/or interfaces with a communication platform including a messaging platform, which functions to enable communication between multiple users and/or between users and entities (e.g., databases, healthcare facility administrators, technical support, etc.). The messaging platform is preferably a secure platform configured to be compliant with healthcare regulations (e.g., Health Insurance Portability and Accountability Act [HIPAA]) and/or any other privacy and/or data security protocols (e.g., encryption protocols).

The messaging platform preferably enables messages (equivalently referred to herein as chats) to be exchanged between users. The communication platform can additionally or alternatively include voice communications (e.g., with a Voice over Internet Protocol [VoIP]), which can function in some cases to still enable communication even when a user loses connection; video communications (e.g., teleconferencing, video consultations, video communications with a sales representative for advice during a procedure, etc.); and/or any other communications. The messaging platform is preferably part of the application, but can additionally or alternatively be a $3^{rd}$ party application in communication with the application, a native application to the mobile device (e.g., text messaging application), and/or any other application.

Additionally or alternatively, the application can be configured for any or all of: case sharing, actionable alerts and notifications sent to users, integrations with $3^{rd}$ party applications and/or systems, and/or any other actions.

In a preferred set of variations, outputs of an analysis of biosignals, along with the analyzed biosignals, are saved on a cloud server and made available on a mobile application and a web portal for review by cardiologists. These interfaces preferably allow the cardiologist to review the identified suspicious ECGs, optionally along with additional information, such as the degree of suspicion of the positive suspected HCM predictions (e.g., LOW, MEDIUM, or HIGH).

4. Method 200

The method 200 functions to check for and/or detect acute conditions, such as acute cardiac conditions (e.g., HCM), thereby enabling participants to be appropriately and timely treated. Additionally or alternatively, the method 200 can function to recommend and/or optimize a set of next steps for the patient, monitor next steps for the patient (e.g., check in on specialist recommendations, detect read receipts that specialists have examined the patient's information, etc.), and/or otherwise assist in triage and/or treatment of the patients.

Figure 4:
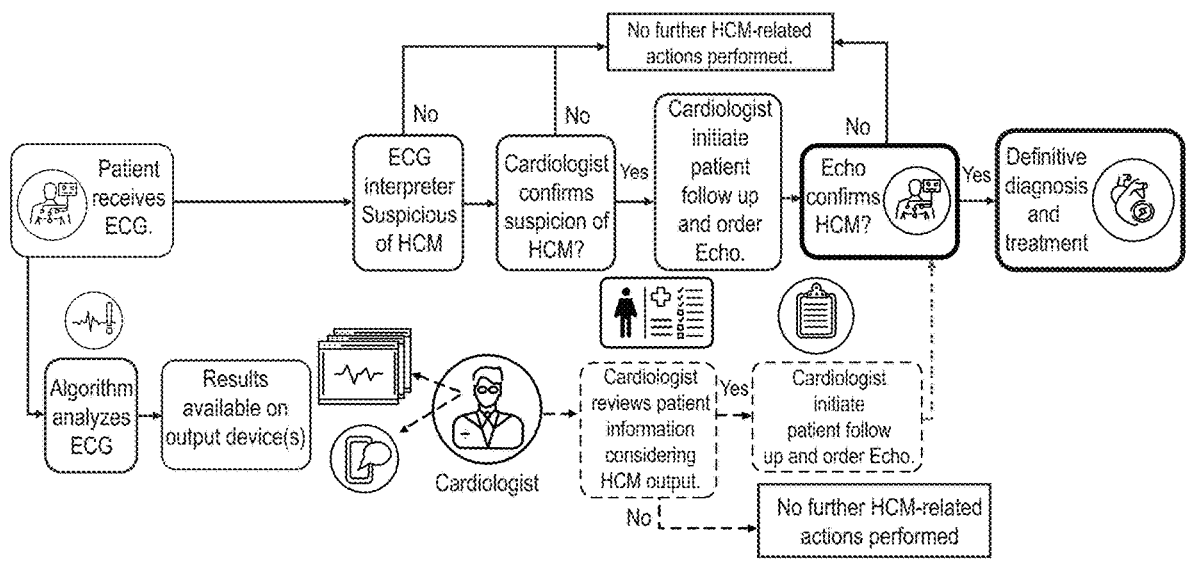
FIG. 4 depicts a schematic variation of a method for cardiac signal processing.

The method is preferably configured to be performed (e.g., in part, in full, etc.) in parallel with conventional standard of care pathways (e.g., as shown in FIG. 4), but can alternatively be performed in absence of such pathways, as part of such pathways, in place of such pathways, and/or can otherwise be suitably performed.

The method is preferably performed in response to generation and/or receipt of input data (e.g., ECG data), such as performed in response to sampling of ECG data at an ECG monitor of (or interfaced with) the system, and/or performed in response to receipt of the sampled ECG data. The method is preferably performed (e.g., independently) for each such input received, more preferably performed once for each such input received (e.g., performed a single time for each ECG sampled and received), but can additionally or alternatively be performed multiple times per input, performed only for a subset of inputs, performed for multiple inputs together, and/or performed with any other suitable numerosity. All or portions of the method can be performed in real time (e.g., responsive to a request), iteratively, concurrently, asynchronously, periodically, and/or at any other suitable time. All or portions of the method can be performed automatically, manually, semi-automatically, and/or otherwise performed.

All or portions of the method can be performed by one or more components of the system, using one or more computing systems, using one or more databases (e.g., a system database, a third-party database, etc.), by one or more users, and/or by any other suitable systems and/or entities. The computing system can include one or more: CPUs, GPUs, custom FPGA/ASICS, microprocessors, servers, cloud computing, and/or any other suitable components. The computing system can be local, remote, distributed, or otherwise arranged relative to any other system or module.

4.1 Method—Receiving a Set of Inputs S100

The method 200 can include receiving a set of inputs S100, which functions to receive information for use in performing any or all of the remaining processes of the method 200.

S100 is preferably performed initially in the method 200, but can additionally or alternatively be performed in response to another process of the method 200, performed multiple times, and/or the method 200 can be performed in absence of S100.

The set of inputs preferably includes a set of biological signals (e.g., bioelectrical signals, biometric signals, etc.) collected from the patient, but can additionally or alternatively include image data (e.g., diagnostic images, images from an echocardiogram, etc.), other diagnostic information, and/or any other information (e.g., demographic information, historical information, etc.) associated with the patient. Additionally or alternatively, the set of inputs can include information from and/or associated with any other users (e.g., cardiac specialists), such as contact information, scheduling availability, workload information, areas and/or treatments of expertise, and/or any other information. Further additionally or alternatively, the set of inputs can include healthcare facility information (e.g., which specialists are on-call, which treatments are able to be performed, etc.), and/or any other information from any suitable sources.

In a preferred set of variations, the set of inputs includes a signal stream from an electrocardiogram (ECG and/or EKG) monitor, such as 12-lead ECG recordings collected as part of a routine clinical assessment. In a set of specific examples, 12-lead ECG sources (e.g., ECG machines or ECG information systems) will be configured to automatically send all ECG recordings (e.g., signal waveforms) acquired during clinical practice to a cloud-based server without user intervention or decision-making (e.g., ECG data forwarding to the cloud server occurs without input, control, and/or confirmation from the non-specialist clinician or practitioner acquiring the ECG signal for use in the standard of care assessment). Additionally or alternatively, the set of inputs can include associated metadata including patient age, patient gender, etc.; and/or technical characteristics such as sampling frequency, lead alignment parameters, voltage units, duration, and number of leads, etc.; and/or any other inputs.

Additionally or alternatively, S100 can include receiving any other inputs.

4.2 Method—Processing the Set of Inputs to Determine a Set of Metrics S200

The method 200 includes processing the set of inputs to determine a set of metrics S200, which functions to determine metrics with which to assess the patient and optionally trigger actions in accordance with the assessment.

S200 is preferably performed in response to and based on the inputs received in S100, but can additionally or alternatively be performed at any other times and/or based on any suitable information.

S200 is preferably performed automatically (e.g., each time an ECG recording is made) with a set of models and/or algorithms, and further preferably at least in part with a set of machine learning algorithms and/or models (e.g., as described above), but can additionally or alternatively be performed with any other tools and/or in response to any suitable triggers.

In a preferred set of variations, S200 is at least partially performed with a set of machine learning algorithms which are trained based on ECG data which corresponds to cases of HCM, other cardiac conditions (e.g., those besides HCM), and no cardiac conditions. Additionally or alternatively, the algorithms and/or models can be trained based on any other data.

S200 can optionally include pre-processing any or all of the set of inputs (e.g., at one or more signal preprocessors and/or validation models, such as described above in more detail regarding the system 100), which can function to: determine whether or not to proceed with subsequent processes of the method, inform which outputs (e.g., notification content) are triggered, prepare the inputs for easier and/or more uniform processing, and/or can perform any other functions. The pre-processing can be performed with any or all of: algorithms and/or models (e.g., machine learning, deep learning, rule-based, etc.), decision trees, lookup tables, filters, signals processing techniques (e.g., normalization), and/or any other tools.

In some variations (e.g., as shown in FIGS. 6A-6D), for instance, pre-processing can include any or all of: converting and/or adjusting (e.g., format conversion, de-identification, normalization, standardization, etc.) the set of inputs (e.g., ECG waveform(s)), such as at a signal transformer of the system; checking the set of inputs (e.g., metadata, ECG waveforms, patient medical records, etc.) against inclusion and/or exclusion criteria (e.g., wherein in an event the data is not suitable for further processing, the algorithm terminates and returns a corresponding error code and an error message so that an appropriate error or warning message can be displayed to the user), such as at a criteria-based filter model; processing the data (e.g., ECG signal) with a quality filter (e.g., classifying the data quality using a quality model), such as a filter that checks whether the study is of acceptable quality for further processing based on the signal content (e.g., noise, amplitude, artifact presence, incomplete data, indicia of missing or faulty leads, etc.), such as at a quality model; reconfiguring (e.g., transforming) the inputs (e.g., ECG signal waveform) into an input format (e.g., for one or more models, such as neural networks) for use downstream in the algorithmic pipeline, such as reconfiguring the inputs into a multi-dimensional representation (e.g., multi-dimensional numerical tensors) and/or an image-based representation (e.g., at one or more reconfiguration elements); and/or any other pre-processing processes (e.g., performed by any other suitable elements of the system 100 and/or of any other systems).

S200 preferably includes processing any or all of the set of inputs (e.g., pre-processed inputs, pre-processed ECG signals, etc.) with a set of machine learning models and/or algorithms, which functions to make a prediction associated with the condition (e.g., HCM) being assessed. The set of machine learning models preferably includes a set (e.g., ensemble) of one or more trained deep neural network models (e.g., convolutional neural networks [CNNs]), where the set (e.g., ensemble) includes one or several models that can optionally differ with respect to any or all of: neural network architecture, weight initialization, training process, training data, and/or any other characteristics.

Figure 6A:
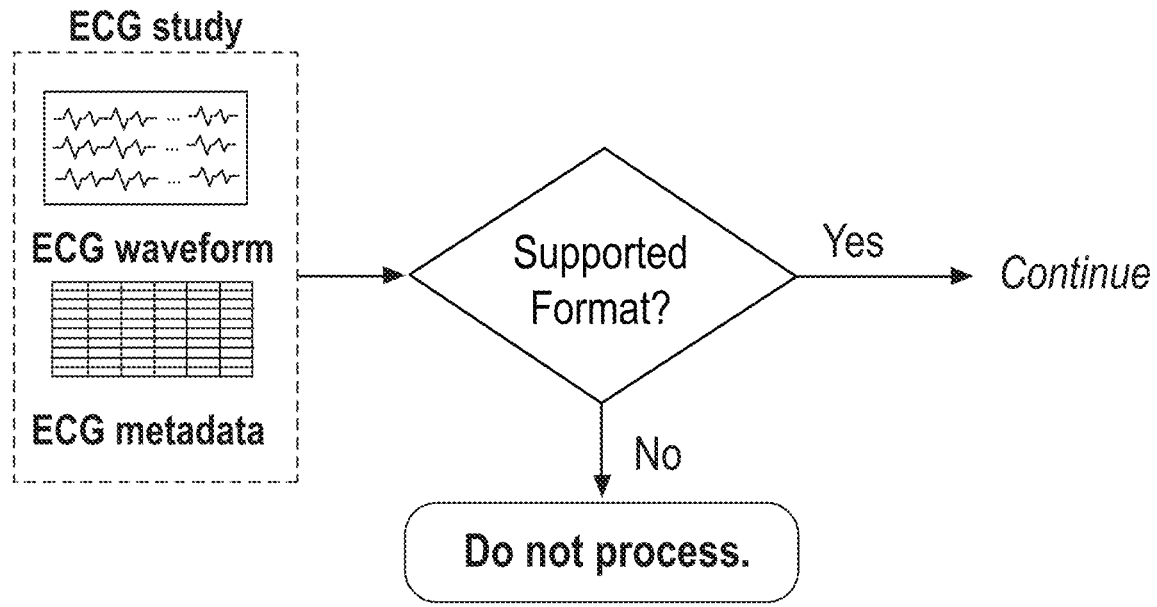
FIGS. 6A-6G depict schematic portions of a variation of a method for cardiac signal processing.
Figure 6B:
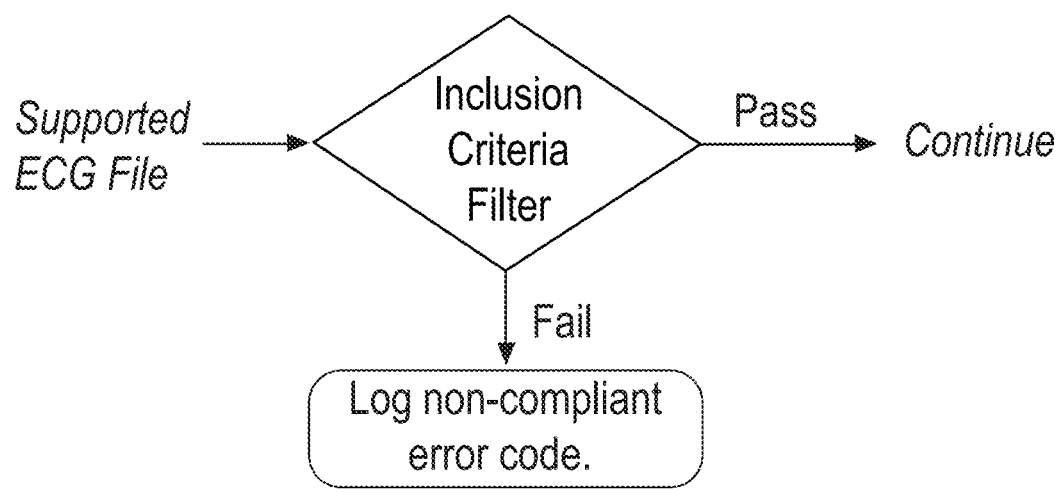
Figure 6C:
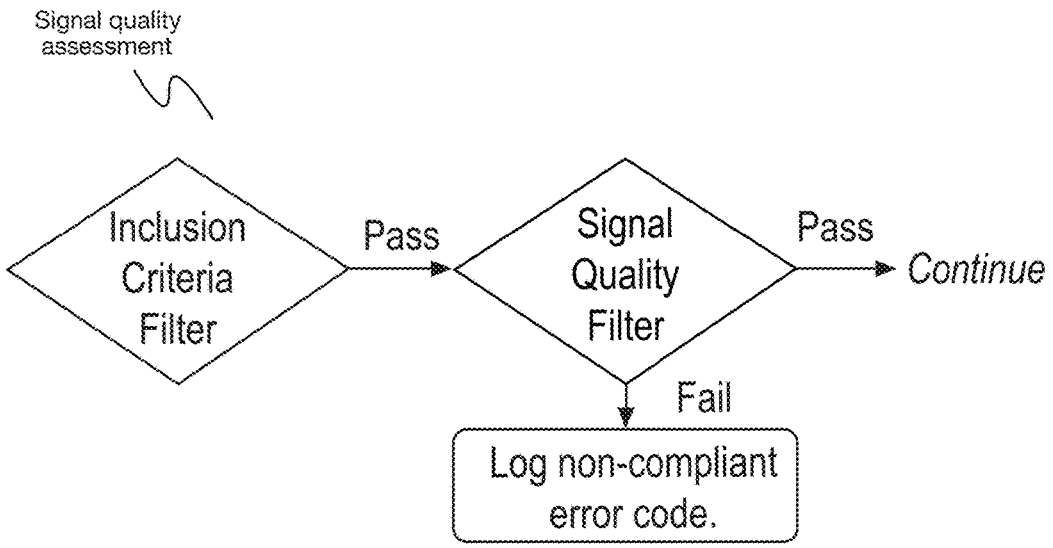
Figure 6D:
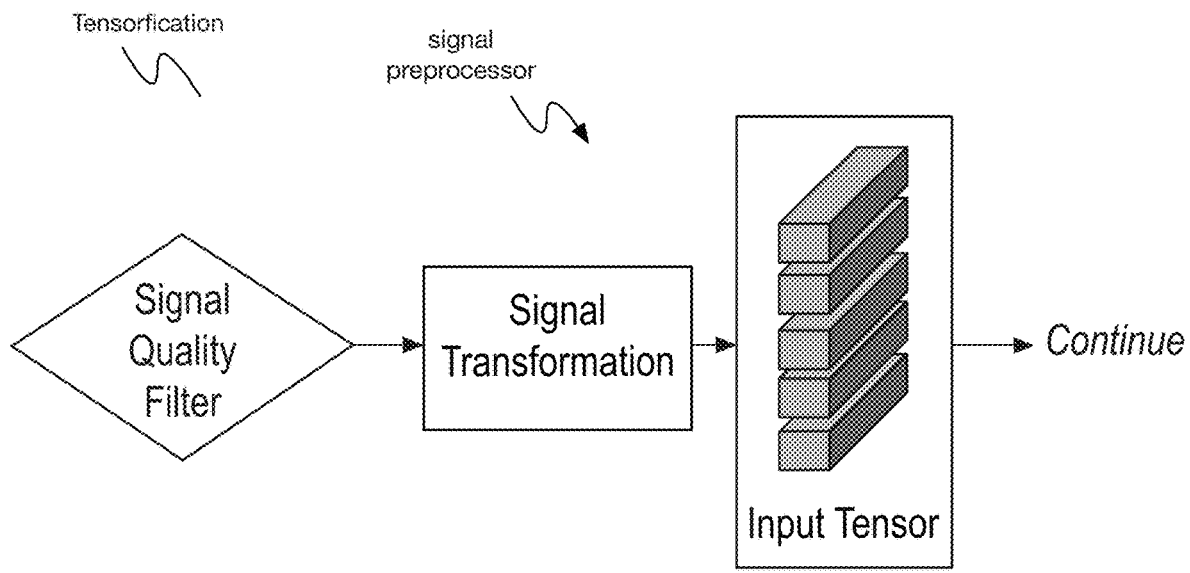
Figure 6E:
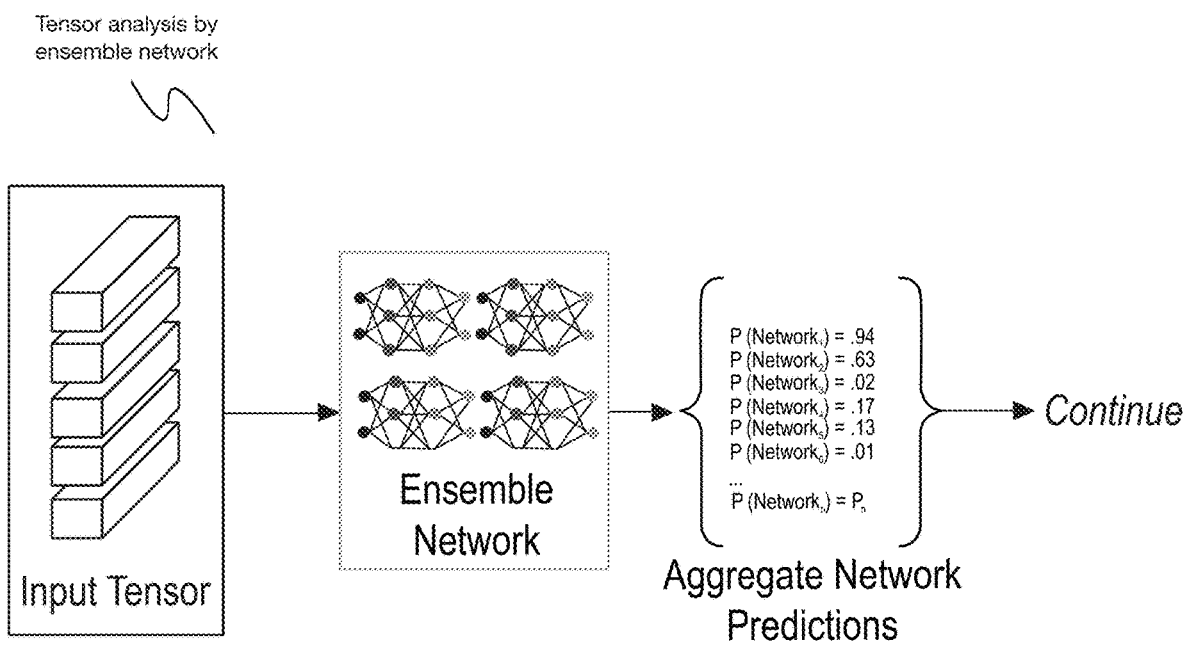

In a preferred set of variations (e.g., as shown in FIG. 6E), a set of input tensors produced based on pre-processing a set of ECG signals (e.g., 12 ECG waveforms) is fed into an ensemble of trained deep neural network models, where each downstream neural network is fed with specific tensor(s) as input corresponding to the network architecture.

S200 can optionally include aggregating a set of intermediate outputs produced by a set of models (e.g., outputs of each of a set of neural networks in an ensemble), comparing the set of intermediate outputs and/or aggregated set of intermediate outputs with a set of thresholds and/or criteria, and/or any other suitable processes.

Figure 6F:
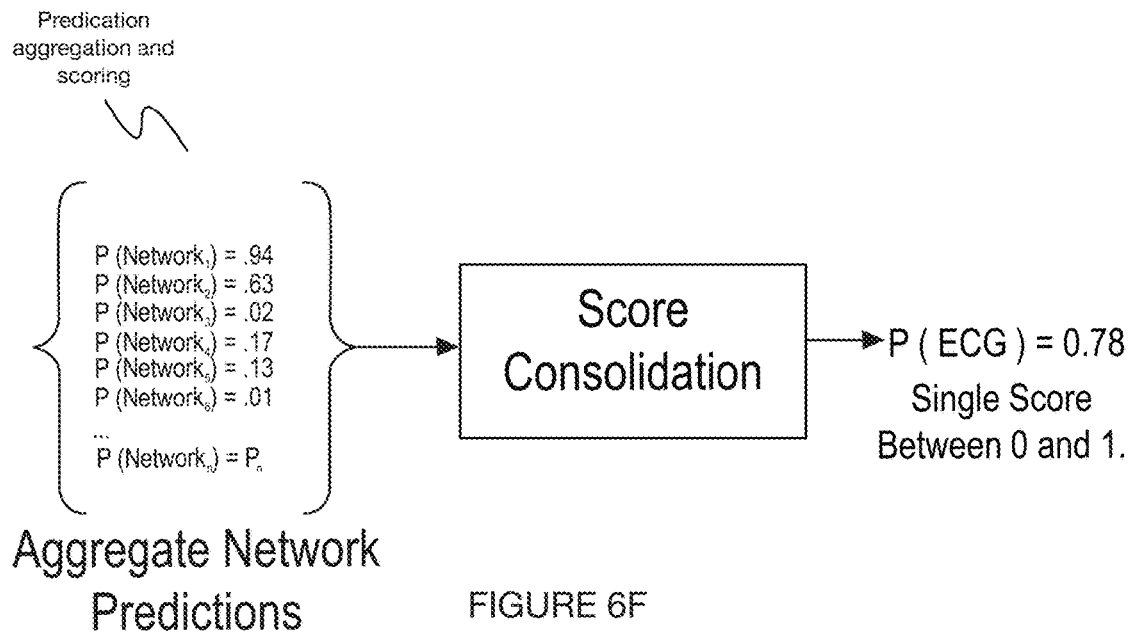

In some variations (e.g., as shown in FIG. 6F), for instance, S200 includes combining (e.g., summing, averaging, summing in a weighted fashion, etc.) predictions from multiple neural network models in an ensemble into a single representative prediction score (e.g., which takes values between 0 and 1). For example, this combining can be performed such as described above in more detail regarding the aggregator, and/or can be performed in any other suitable manner.

Figure 6G:
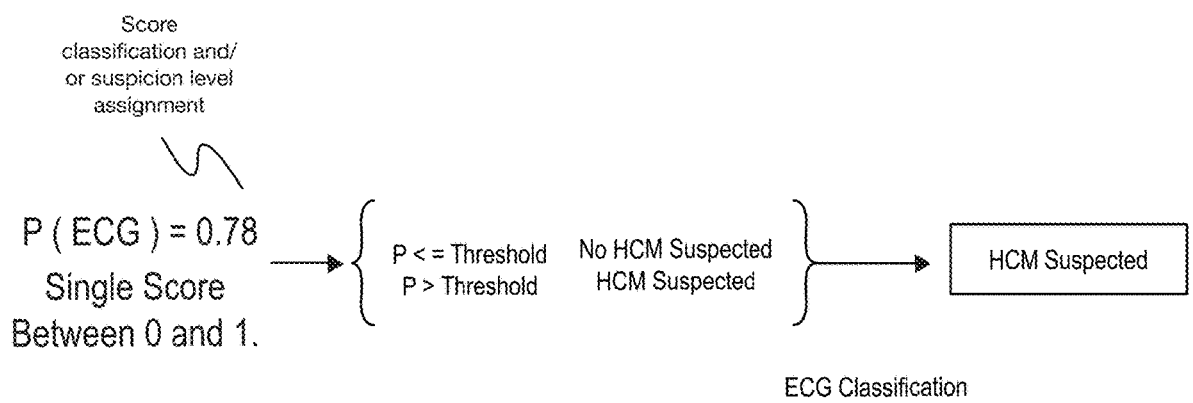

The algorithm output of S200 is preferably a binary decision indicating the presence or absence of the suspected HCM (and optionally a suspicion level as described in S300), wherein the binary decision can be obtained by applying a decision threshold (cut-off) to the model prediction score. In some variations (e.g., as shown in FIG. 6G), for instance, the aggregated score and/or multiple score values are compared with a set of thresholds, where score values falling above the threshold will trigger a "positive" result indicative of a suspected condition (e.g., suspected HCM), while scores falling below the threshold (e.g., including the threshold itself) will trigger a "negative" result indicative of no suspected condition (e.g., suspected HCM).

Additionally or alternatively, the set of outputs can include non-binary outputs and/or any other outputs.

Figure 5A:
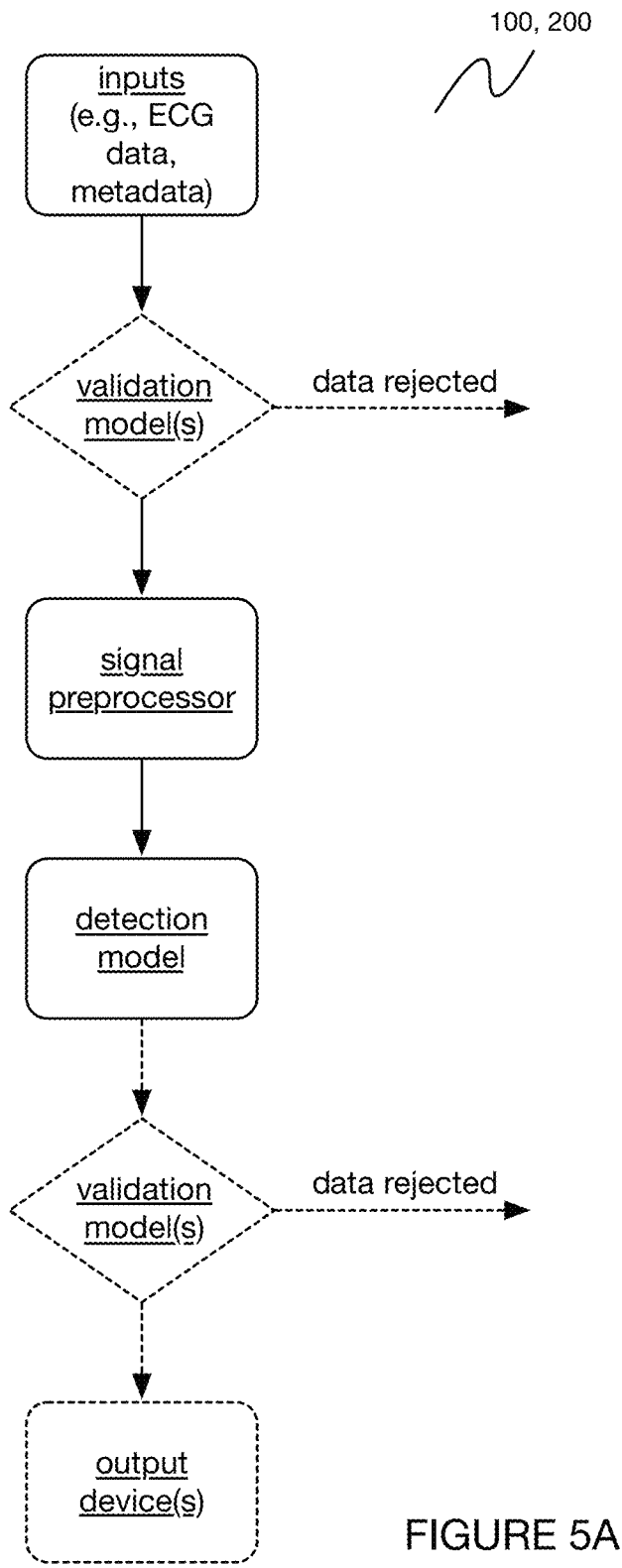
FIGS. 5A-5B depict a first and second schematic variation, respectively, of a method and associated system for cardiac signal processing.
Figure 5B:
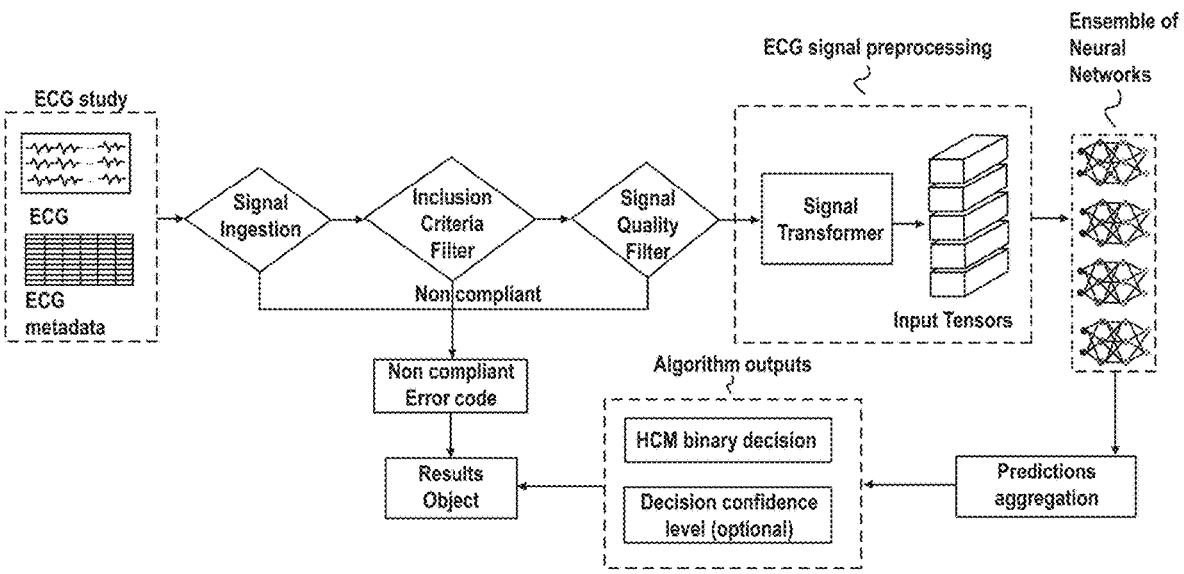

In some examples (e.g., as shown in FIGS. 5A and/or 5B), S200 includes: filtering the received signals using one or more criteria-based models (e.g., "inclusion criteria filter) and/or quality models (e.g., "signal quality filter"), wherein some of the received signals may be rejected, then preprocessing the filtered signals that were not rejected (e.g., at a signal preprocessor), such as by transforming and/or reconfiguring the signals, and then by performing detection on the preprocessed signals (e.g., at the detection model, such as in parallel at a plurality of sub-models thereof followed by aggregation of the outputs of the different sub-models). In some such examples, further filtering may then be performed (e.g., only for positive predictions from the detection model) based on medical history (e.g., at a medical history model), such as filtering out detections associated with diagnoses for which false positives are more likely (e.g., as described above in more detail regarding the medical history model). However, S200 can additionally or alternatively include processing the set of inputs in any other suitable manner.

4.3 Method—Determining a Set of Supplementary Metrics Associated with the Set of Metrics S300

The method 200 can include determining a set of supplementary metrics associated with the set of metrics S300, which functions to provide additional information with which to assess the patient, inform treatment and/or other next steps for the patient, prevent wasted time of specialists in assessing false positive determinations, prevent notification fatigue (e.g., the ignoring of notifications by a specialist who is flooded with notifications and/or receives a high percentage of notifications corresponding to false positive results), and/or can perform any other functions.

In a preferred set of variations, S300 further functions to enable actionable outputs (e.g., notifications) to be triggered in accordance with a confidence level associated with a positive determination indicated that the condition is suspected for the patient. In specific examples involving low prevalence conditions (e.g., HCM), this can function to still enable positive cases to be detected, while indicating which detections in particular have a higher likelihood of being a false positive (e.g., so the specialist can prioritize patients, recommend treatment options in accordance with these confidence levels, etc.).

S300 is preferably performed as part of (e.g., contemporaneously with, overlapping with, at least partially overlapping with, etc.) S200, wherein the set of supplementary metrics is produced as an output of any or all of a set of models and/or algorithms (e.g., together with the set of outputs, as part of the set of outputs, etc.). In a preferred set of variations, for instance, S300 is performed in response to determining a positive result in S200 wherein the set of supplementary metrics is determined based on the set of scores (e.g., aggregated score, multiple scores, etc.) produced in S200. Additionally or alternatively, any or all of the set of supplementary metrics can be produced outside of S200 (e.g., in response to S200), in absence of S200, based on a different set of models and/or algorithms and/or other tools (e.g., rule-based logic, decision trees, lookup tables, etc.) than used in S200, and/or at any other times.

The set of supplementary metrics preferably includes a confidence metric (equivalently referred to herein as a confidence level, suspicion level, and/or suspicion metric) associated with each of the scores that indicate that the condition is suspected to be present, wherein the confidence metric represents the confidence associated with that positive determination. Additionally or alternatively, a confidence metric can be determined for and/or associated with other and/or all scores (e.g., negative determinations), determined independently of scores, and/or otherwise determined or reflective of any information.

Figure 7:
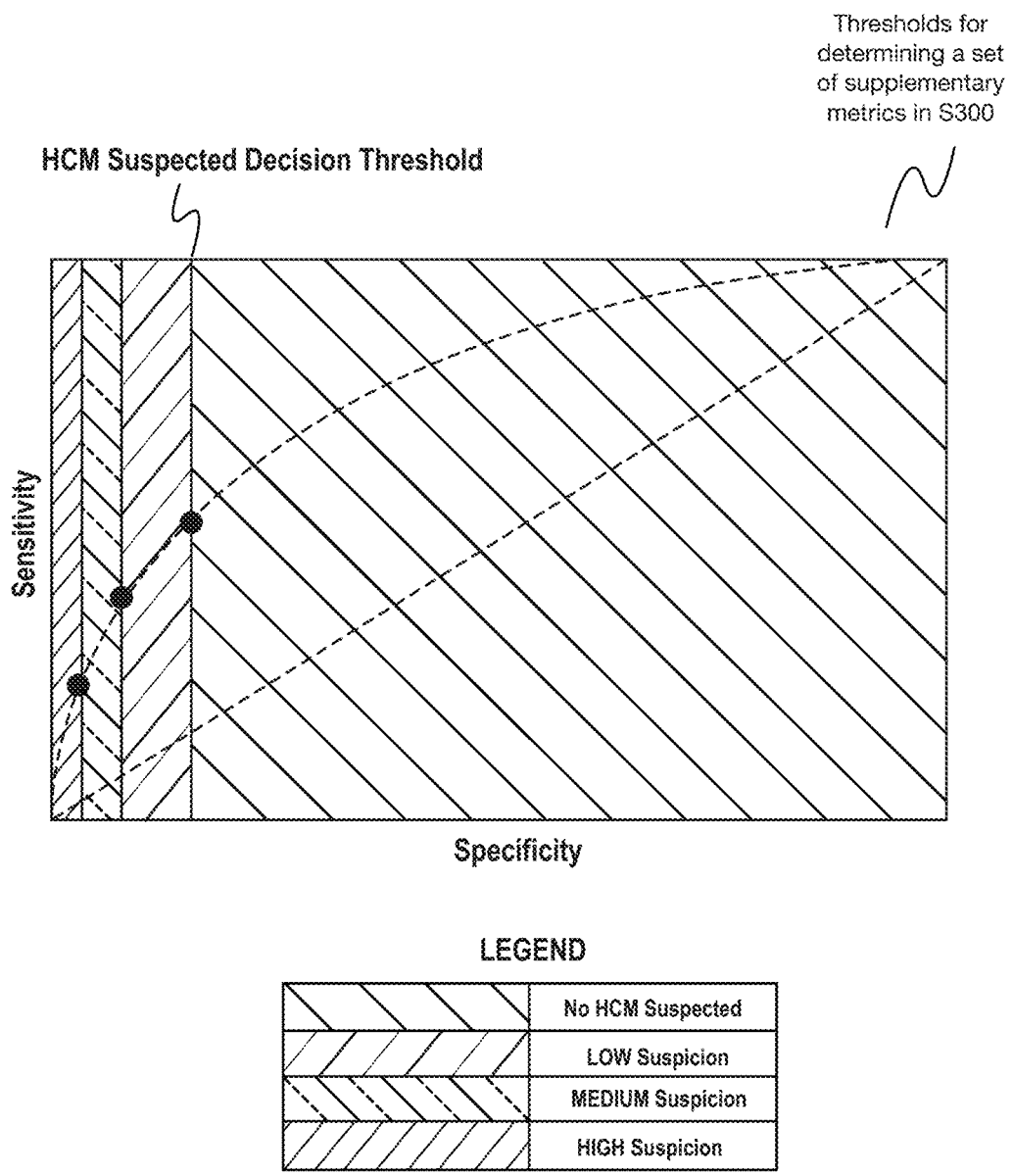
FIG. 7 is a demonstrative example of a set of multiple suspicion levels used in a variation of a method for cardiac signal processing.

In a preferred set of variations, the aggregated score associated with a positive result (resulting indicating that the condition is suspected) is compared with a set of thresholds (e.g., multiple thresholds), wherein the confidence metric is determined based on the comparison. In a set of specific examples (e.g., as shown in FIG. 7), for instance, the set of thresholds are determined in accordance with a nonlinear curve representing a sensitivity versus specificity associated with a positive determination, such that varying levels of confidence which correspond to differing levels of sensitivity and/or specificity can be attributed to the aggregated score.

The confidence metric can correspond to (e.g., represent, include, etc.) any or all of: a binary classification (e.g., high vs. low confidence), one of a set of multiple classifications (e.g., high vs. medium vs. low), a spectrum of confidence levels (e.g., include a score along a spectrum of possible values), and/or can be otherwise suitably represented.

In a set of variations (e.g., as shown in FIG. 9), a "positive" result indicative of a suspected condition (e.g., HCM) is further assigned a suspicion level of "low," "medium," or "high" based on how far the corresponding prediction score (e.g., aggregated score in S200) is from the decision threshold. The further that the prediction score is from the threshold, the more certain the finding for the suspected condition.

In a set of examples, for instance: a "low" suspicion level can trigger a more conservative (e.g., lower urgency) set of actions and/or outputs (e.g., notify recipients with a high tolerance for false positives who will adopt and be engaged with a positive predictive value [PPV] as low as 10-20%, given their interest in studying and treating the disease, mimics, taking a conservative approach to reviewing more patients, and/or building their practice around it); a "medium" suspicion level can trigger a less conservative set of actions and/or outputs than the "low" suspicion level (e.g., allow users to explore and review the most confident predictions [e.g., those identified as "high" suspicion] along with those additional inputs [e.g., ECGs] with a reasonably confident prediction of the suspected condition whilst avoiding the "low" suspicion inputs which will yield a much higher false positive rate); and a "high: suspicion level which can be communicated to users who only want and/or have the bandwidth to review the most confident predictions.

Additionally or alternatively, any other supplementary metrics can be used and/or determined in any suitable way(s).

4.4 Method—Determining a Set of Outputs Based on the Set of Metrics and/or the Supplementary Set of Metrics S400

The method 200 can include determining a set of outputs based on the set of metrics and/or the supplementary set of metrics S400, which functions to trigger an appropriate (e.g., optimal) action (e.g., in S500) in response to the set of metrics and/or supplementary set of metrics. Additionally or alternatively, S400 can function to determine outputs which reduce notification fatigue of users as caused by frequent false positive notifications (e.g., leading to them ignoring similar future notifications); determine outputs which are most actionable based on the particular metrics; direct outputs to optimal recipients (e.g., those best suited to treat the patient) and/or at optimal times; and/or can perform any other functions.

S400 is preferably performed in response to S200, and optionally further in response to S300, but can additionally or alternatively be performed in response to another process of the method 200, and/or at any other times. Alternatively, the method 200 can be performed in absence of S400 (e.g., in an event that no detection of the condition is determined in S300).

In a preferred set of variations, in an event that a positive detection of a condition is made (e.g., HCM detected/suspected), the set of outputs determined in S400 is determined based on this positive detection and further preferably based on a confidence level associated with the positive detection. Additionally or alternatively, the outputs can be determined based on: recipient information (e.g., schedule, expertise, availability, current workload and/or number of outputs provided recently, etc.) and/or preferences (e.g., which suspicion level cutoff they prefer), facility information (e.g., specialist schedules, number of beds available, etc.), and/or any other information.

In examples, this can include determining any all of the following based on the positive detection and/or confidence level: who the particular recipients of the outputs are (e.g., cardiac specialist currently on-call for a "high" confidence level vs. private practice cardiologist for "low" confidence, how many recipients are notified, etc.); temporal parameters associated with the output (e.g., when the output is provided, how frequently the system checks in for a read receipt and/or confirmed next steps for the patient from the recipient, etc.); a ranked list to be provided to a recipient (e.g., with higher priority patients corresponding to higher confidence levels in the list); a type of output (e.g., message vs. call, audio alert vs. visual alert, etc.) provided to the recipient; whether or not a second recipient should be triggered if the first recipient does not respond and/or provide acknowledgement of receipt (e.g., read receipt) of the output within a predetermined threshold and/or what value the predetermined threshold should have; and/or any other determinations.

Additionally or alternatively, S400 can be otherwise suitably performed.

4.5 Method—Triggering the Set of Outputs S500

The method 200 can include triggering the set of outputs S500, which can function to: facilitate review of the detections made in S300, facilitate treatment and/or the determination of next steps for the patient, and/or can perform any other functions.

S500 is preferably performed in response to and based on S400, but can additionally or alternatively be performed during S400, in response to another process of the method 200, and/or at any other suitable time(s).

The set of outputs can be triggered at any or all of: one or more applications executing on an output device (e.g., mobile user device of a recipient, personal mobile user device of a recipient, workstation, etc.); one or more output devices (e.g., absent of an application); and/or at any other user interfaces.

In a preferred set of variations, software outputs (e.g., messages, alerts, calls, etc.) are made available to a specialist (e.g., cardiologist) or other recipient through web-based or mobile software interfaces, where the software outputs inform the recipient of patients associated with the suspected condition. In specific examples involving ECG, the software outputs are intended to inform the cardiologist of ECGs for further review and can be used on an advisory basis as part of a broader patient assessment performed by the cardiologist that takes into consideration patient demographics, clinical history, and other relevant patient information in conjunction with physician's knowledge of ECG patterns and clinical expertise in the determination for further HCM patient follow up.

Figure 8A:
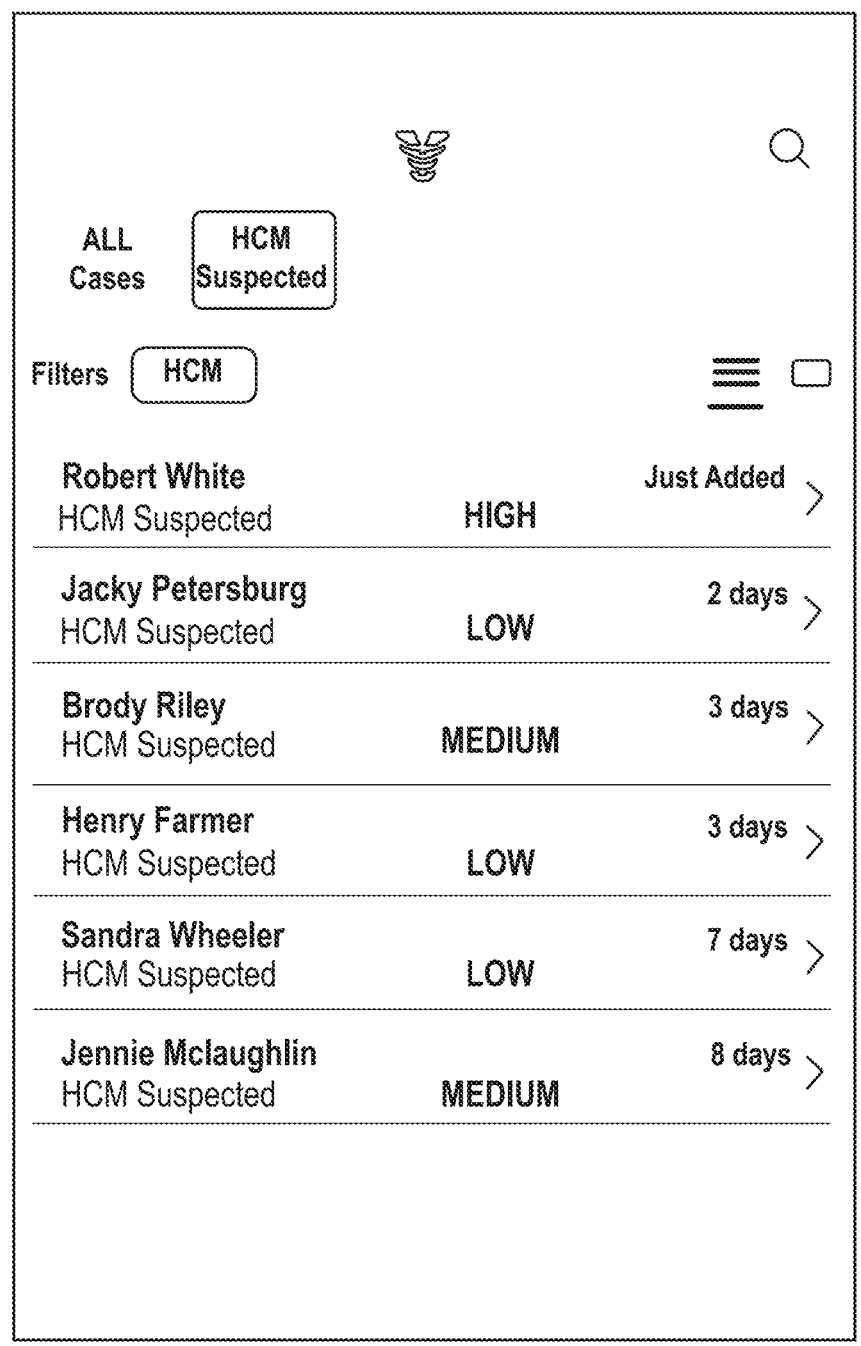
FIGS. 8A-8C depict a specific example of a set of outputs provided to a user.
Figure 8B:
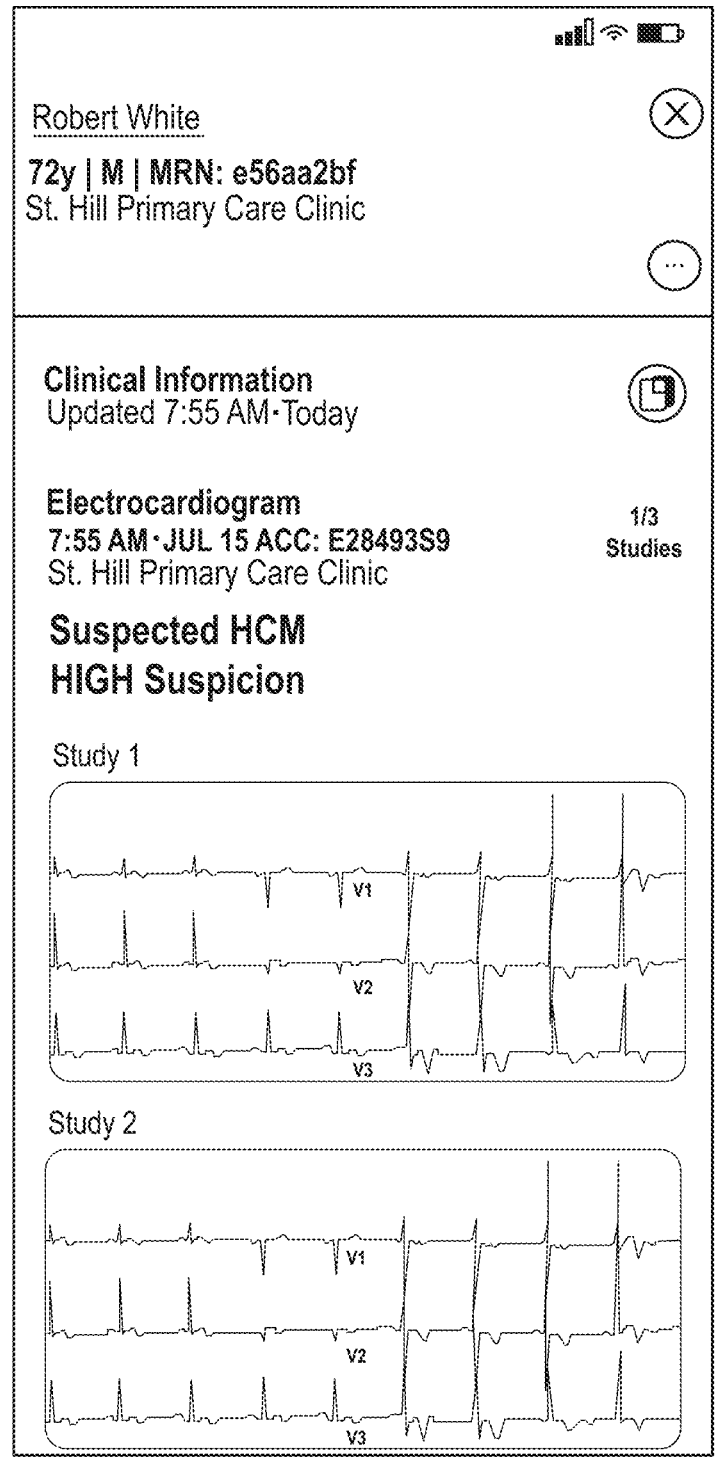
Figure 8C:
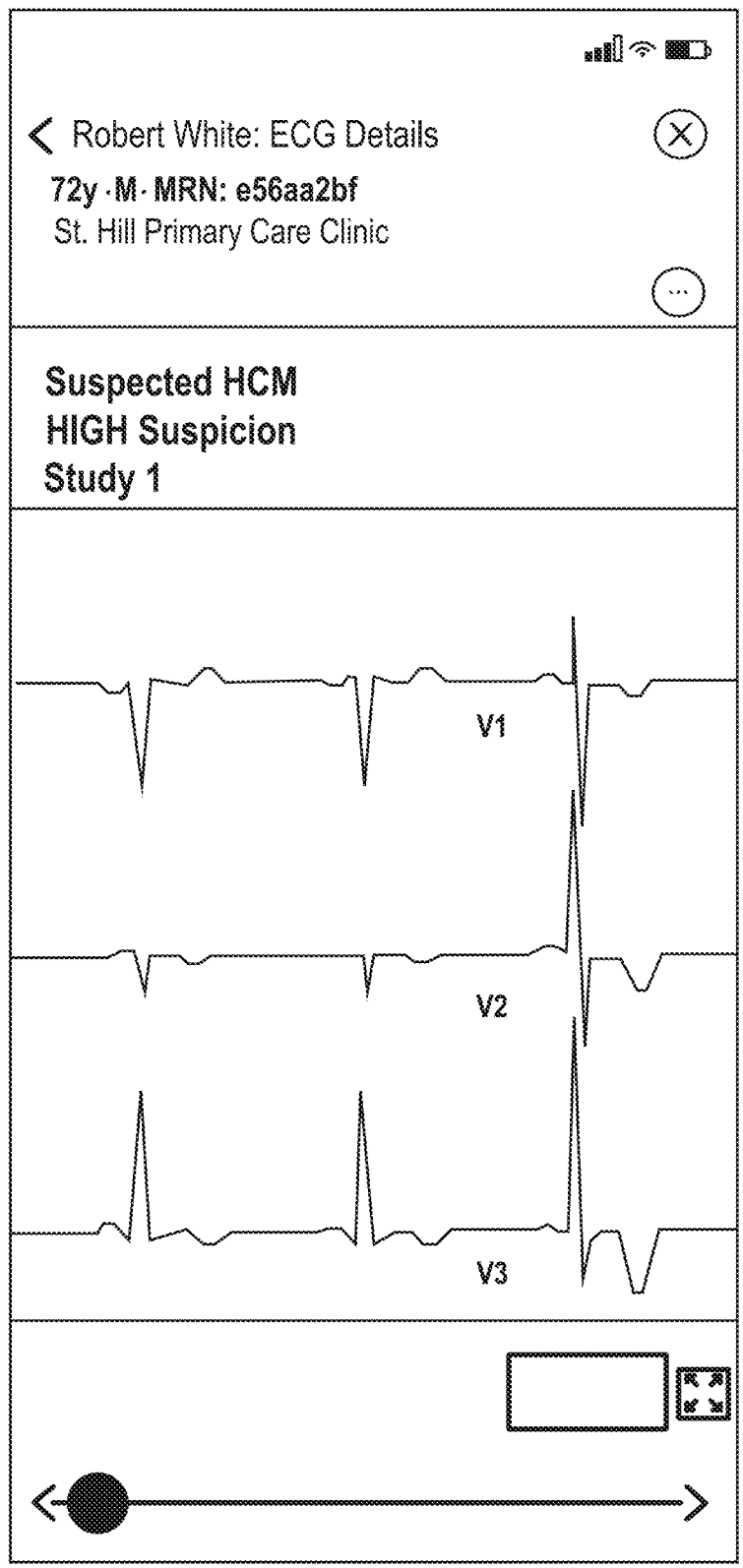

FIGS. 8A-8C demonstrate an example of the device results as displayed through a mobile application. A list of patients with suspected HCM for cardiologist review as determined by the software algorithm (FIG. 8A), the patient overview screen showing suspicion level and the ECG signals available for review (FIG. 8B), and a single ECG signal being viewed through the mobile application interface (FIG. 8C).

In some examples, the software outputs can be provided to the user (e.g., cardiologist) in association with one or more additional outputs (e.g., outputs associated with the same patient). In a first example, an ECG alert associated with a patient may be presented in association with other medical information associated with the patient, such as the patient ECG, patient echocardiogram imaging and/or associated report(s), and/or any other suitable patient medical records and/or other information. In a second example, an ECG alert associated with a patient may additionally or alternatively be presented in association with a module configured to enable referral of the patient to a medical specialist (e.g., specialist specializing in diagnosis, treatment, and/or other care associated with the specific medical condition, such as a cardiologist specializing in HCM), such as wherein the user may initiate a patient referral to one or more relevant specialists via this module. However, the software outputs can additionally or alternatively be provided in association with any other suitable outputs.

Additionally or alternatively, the method 200 can include any other suitable processes.

All references cited herein are incorporated by reference in their entirety, except to the extent that the incorporated material is inconsistent with the express disclosure herein, in which case the language in this disclosure controls.

Different subsystems and/or modules discussed above can be operated and controlled by the same or different entities. In the latter variants, different subsystems can communicate via: APIs (e.g., using API requests and responses, API keys, etc.), requests, and/or other communication channels. Communications between systems can be encrypted (e.g., using symmetric or asymmetric keys), signed, and/or otherwise authenticated or authorized.

Alternative embodiments implement the above methods and/or processing modules in non-transitory computer-readable media, storing computer-readable instructions that, when executed by a processing system, cause the processing system to perform the method(s) discussed herein. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

We claim:

1. A method for cardiac signal processing, comprising:
receiving electrocardiogram (ECG) data associated with a patient;
determining that the ECG data is valid for use with a trained detection model, comprising providing the ECG data to a trained quality model, wherein the trained quality model is trained to detect low quality input data within the ECG data based on a set of quality indices, wherein the low quality input data is not valid for use with the trained detection model, wherein the trained detection model is associated with detection of a medical condition;
transforming the ECG data into a detection model input for the trained detection model;
at the trained detection model, determining a prediction metric based on the detection model input, wherein the prediction metric is indicative of a likelihood that the patient has the medical condition;
determining that the prediction metric is greater than a threshold value;
in response to determining that the prediction metric is greater than the threshold value, based on the prediction metric, determining an output indicative of the patient and the medical condition; and
providing the output to a user.

2. The method of claim 1, wherein the medical condition is hypertrophic cardiomyopathy.

3. The method of claim 1, wherein determining the prediction metric is performed in response to determining that the ECG data is valid for use with the trained detection model.

4. The method of claim 3, further comprising:
receiving second ECG data associated with a second patient;
determining that the second ECG data is not valid for use with the trained detection model, comprising providing the second ECG data to the trained quality model; and
in response to determining that the second ECG data is not valid for use with the trained detection model, not determining a prediction metric based on the detection model input.

5. The method of claim 4, wherein:
determining that the ECG data is valid for use with the trained detection model further comprises, at the trained quality model, classifying the ECG data as valid; and
determining that the second ECG data is not valid for use with the trained detection model further comprises, at the trained quality model, classifying the second ECG data as not valid.

6. The method of claim 1, further comprising:
receiving a second ECG data associated with a second patient;
determining that the second ECG data is valid for use with the trained detection model, comprising providing the second ECG data to the trained quality model;
transforming the second ECG data into a second detection model input for the trained detection model; and
at the trained detection model, determining a second prediction metric based on the second detection model input, wherein the second prediction metric is indicative of a likelihood that the second patient has the medical condition.

7. The method of claim 6, further comprising:
determining that the second prediction metric is greater than the threshold value;
in response to determining that the second prediction metric is greater than the threshold value, based on the second prediction metric, determining a second output indicative of the second patient and the medical condition; and
providing the second output to a second user.

8. The method of claim 6, further comprising determining that the second prediction metric is less than the threshold value.

9. The method of claim 1, further comprising training the trained quality model using a labeled ECG dataset, wherein the labeled ECG dataset comprises a first subset associated with a valid label and a second subset associated with an invalid label.

10. The method of claim 9, wherein ECG data of the second subset is indicative of noise greater than a threshold noise level.

11. The method of claim 9, wherein ECG data of the second subset is indicative of a missing lead.

12. The method of claim 9, wherein ECG data of the second subset is indicative of presence of a pacemaker.

13. The method of claim 1, further comprising receiving metadata in association with the ECG data, wherein determining that the ECG data is valid for use with the trained detection model further comprises assessing the metadata based on a set of one or more metadata criteria.

14. The method of claim 13, wherein the set of one or more metadata criteria comprises a minimum patient age.

15. The method of claim 13, wherein the set of one or more metadata criteria comprises a minimum ECG duration.

16. The method of claim 1, further comprising receiving metadata in association with the patient, the metadata indicative of a set of medical diagnoses associated with the patient, wherein determining that the ECG data is valid for use with the trained detection model further comprises determining that the set of medical diagnoses is disjoint from a set of excluded diagnoses.

17. The method of claim 16, wherein the set of excluded diagnoses comprises at least one diagnosis selected from the group consisting of: hypertensive disease, valve disease, non-HCM left ventricular hypertrophy, non-HCM cardiomyopathy, amyloidosis, Anderson-Fabry disease, and Friedreich ataxia.

18. The method of claim 16, wherein:
determining that the ECG data is valid for use with the trained detection model further comprises, at the trained quality model, classifying the ECG data as valid; and
determining the prediction metric based on the detection model input is performed in response to classifying the ECG data as valid.

19. The method of claim 18, wherein determining that the set of medical diagnoses is disjoint from the set of excluded diagnoses is performed in response to determining that the prediction metric is greater than the threshold value.

20. The method of claim 1, wherein:
the trained detection model comprises:
an ensemble of trained neural networks; and
an aggregator; and
determining the prediction metric comprises:
at each trained neural network of the ensemble, generating a respective output value and providing the respective output value to the aggregator; and
at the aggregator, determining the prediction metric based on the respective output values.

* * * * *